United States Patent [19]
Compans et al.

[11] Patent Number: 5,843,451
[45] Date of Patent: *Dec. 1, 1998

[54] INTRANASAL IMMUNIZATION AGAINST VIRAL INFECTION USING VIRAL GLYCOPROTEIN SUBUNIT VACCINE

[75] Inventors: Richard W. Compans, Helena; Ranjit Ray, Birmingham, both of Ala.

[73] Assignee: Vaxcel, Inc., Norcross, Ga.

[*] Notice: The term of this patent shall not extend beyond the expiration date of Pat. No. 5,427,782.

[21] Appl. No.: 728,735

[22] Filed: Oct. 11, 1996

Related U.S. Application Data

[63] Continuation of Ser. No. 285,788, Aug. 4, 1994, abandoned, which is a continuation of Ser. No. 887,130, May 20, 1992, Pat. No. 5,427,782, which is a continuation of Ser. No. 574,392, Aug. 27, 1990, abandoned, which is a continuation of Ser. No. 46,820, May 5, 1987, abandoned.

[51] Int. Cl.$^6$ .................. A61K 39/00; A61K 39/155; A61K 39/12; C12N 7/00
[52] U.S. Cl. .................. 424/192.1; 424/204.1; 424/211.1; 424/212.1; 424/214.1; 435/235.1; 435/172.1; 514/8; 530/806
[58] Field of Search .................. 424/192.1, 204.1, 424/211.1, 212.1, 214.1; 435/235.1, 172.1; 514/8; 530/806

[56] References Cited

U.S. PATENT DOCUMENTS

| | | | |
|---|---|---|---|
| 3,544,680 | 12/1970 | Plotkin | 424/210.1 |
| 3,634,587 | 1/1972 | Ament et al. | 424/210.1 |
| 3,927,208 | 12/1975 | Zygraich et al. | 424/233.1 |
| 3,950,512 | 4/1976 | Emery et al. | 424/201.1 |
| 3,953,592 | 4/1976 | Peetermans | 424/206.1 |
| 3,962,421 | 6/1976 | Neurath | 424/210.1 |
| 3,962,422 | 6/1976 | Parks | 424/210.1 |
| 3,962,423 | 6/1976 | Peetermans et al. | 424/206.1 |
| 4,110,433 | 8/1978 | Purdy, III | 424/229.1 |
| 4,132,775 | 1/1979 | Volenec et al. | 424/229.1 |
| 4,172,124 | 10/1979 | Koprowski et al. | 435/70.21 |
| 4,196,265 | 4/1980 | Koprowski et al. | 435/70.21 |
| 4,235,871 | 11/1980 | Papabadjopoulos et al. | 424/450 |
| 4,261,975 | 4/1981 | Fullerton et al. | 424/450 |
| 4,303,644 | 12/1981 | Davis | 424/201.1 |
| 4,318,903 | 3/1982 | Lobmann et al. | 424/206.1 |
| 4,337,314 | 6/1982 | Oeschger et al. | 435/252.1 |
| 4,344,935 | 8/1982 | Leclerc et al. | 424/210.1 |
| 4,356,169 | 10/1982 | Simons et al. | 424/209.1 |
| 4,448,765 | 5/1984 | Ash et al. | 424/450 |
| 4,512,972 | 4/1985 | Schmidt-Ruppin | 424/209.1 |
| 4,522,809 | 6/1985 | Adamowicz et al. | 424/210.1 |
| 4,552,758 | 11/1985 | Murphy et al. | 424/206.1 |
| 4,663,161 | 5/1987 | Mannino et al. | 424/450 |
| 4,790,987 | 12/1988 | Compans et al. | 424/196.11 |
| 5,152,981 | 10/1992 | Rones et al. | 424/214.1 |
| 5,223,254 | 6/1993 | Paradiso et al. | 424/186.1 |
| 5,427,782 | 6/1995 | Compans et al. | 424/192.1 |

FOREIGN PATENT DOCUMENTS

| | | |
|---|---|---|
| 1158978 | 12/1983 | Canada . |
| 0363414 | 4/1988 | European Pat. Off. . |
| 8808718 | 11/1988 | WIPO . |

OTHER PUBLICATIONS

H. Ito and M. Matumoto, Japan. J. Exp. Med., 56 125–129 (1986).
O.G. Andzhaparidza et al., Voprosy Virusologil, "Soviet Progress in Virology", No. 1, 1987, Protective Effect of Virosomes, Containing Influenza Virus Antigens, After Intranasal Administration, pp. 112–114.
Miyamae et al., Microbiol. Immunol., 30(3): 213–223 (1986).
Waldman et al., Nature, 218: 594–95 (1968).
Waldman et al., Am. J. Epidem., 91(6): 575–584 (1970).
Fukumi et al., Dev. Biol. Stand., 33: 155–161 (1976).
Zahradnik et al., J. Med. Virol., 11: 277–285 (1983).
Petrescu et al., Rev. Roum. Med., 35: 307–314 (1984).
Wigley et al., New England J. Med., 283: 1250–1253 (1970).
Morein et al., Nature, 276: 715–718 (1978).
Morein et al., Vaccine, 3 83–93 (1985).
Ray et al., J. Infect. Dis., 152: 1219–30 (1985).
Morein et al., J. Gen. Virol., 64 1557–69 (1983).
Ray et al., Virology, 148: 232–36 (1986).
Ray et al., J. Gen. Virol., 68: 409–18 (1987).
G. Kohler and C. Milstein, Nature, 256: 495–497 (1975).
Kohler et al, European J. of Immunology, 6: 511–19 (1986).
Ray et al., Intransal Immunization with Envelope Glycoproteins of Human Parainfluenza Virus Type 3, pp. 1–26.
Chem. Abs., vol. 72, Abs. No. 53248e (1970).

*Primary Examiner*—Ponnathapura Achutamurthy
*Assistant Examiner*—Padmashri Ponnaluri
*Attorney, Agent, or Firm*—Dann, Dorfman, Herrell and Skillman

[57] ABSTRACT

Method for immunizing against viral infection by administering intranasally an immunogenically effective amount of a viral envelope subunit vaccine comprising a glycoprotein complexed with a lipid.

6 Claims, 2 Drawing Sheets

INTRANASAL IMMUNIZATION AGAINST VIRAL INFECTION USING VIRAL GLYCOPROTEIN SUBUNIT VACCINE

This is a continuation of U.S. patent application Ser. No. 08/285,788, filed Aug. 4, 1994, now abandoned which is a continuation of U.S. patent application Ser. No. 07/887,130, filed May 20, 1992, now U.S. Pat. No. 5,427,782 issued Jun. 27, 1995, which is a continuation of U.S. application Ser. No. 07/574,392, filed Aug. 27, 1990, now abandoned which is a continuation of U.S. application Ser. No. 07/046,820, filed May 5, 1987 now abandoned.

This invention was made with government support under contracts N 43 AI 52604 and N01 AI 62604, awarded by the National Institutes of Health. The government has certain rights in the invention.

BACKGROUND OF THE INVENTION

Parainfluenza viruses are members of the paramyxovirus group, which also includes mumps and Newcastle disease viruses. Human parainfluenza type 3 (PI3: hemadsorption type 1) virus, which is probably the most common among the parainfluenza viruses, causes severe respiratory disease, particularly in children. Parainfluenza viruses type 1 and type 2 have similar epidemiological patterns and often cause croup in children between 1 and 4 years of age. Antigenic relationships have been reported among parainfluenza viruses types 1–4 and also between parainfluenza and mumps viruses, although limited information has been obtained about the protein components involved.

Attempts to vaccinate children against parainfluenza viral infection with formalin-inactivated virus have been reported in the past, but such preparations did not offer effective protection. The results of subsequent studies concerning immunization against paramyxoviruses tend to indicate that inactivation of the virus by chemical treatment probably destroys some of the important antigenic sites responsible for induction of a protective immune response.

Immunization against respiratory tract pathogens has also been proposed using a modified live virus. Administration of attenuated virus has been attempted intranasally as well as through more conventional routes e.g. subcutaneously, intraperitoneally, intramuscularly or intravenously. The elicitation of an immune response through intranasal administration of attenuated virus cannot be considered unexpected in such cases, because the modified live virus of the vaccine is following the natural route of infection of the wild-type virus, creating immunity through a sub-clinical infection. The use of modified live virus to effect immunization entails certain risk, however, in that the avirulent but still active virus may revert to its virulent state after administration to the recipient.

It has previously been documented that envelope glycoproteins, HN and F, of paramyxoviruses are responsible for initiation and progress of the infection process. Studies have shown that antibodies to these glycoproteins are effective in preventing infection.

We previously reported the discovery that a new viral subunit vaccine derived from human parainfluenza type 3 virus envelope glycoproteins complexed with lipid is capable of inducing an antibody response which is far superior to that obtained with the previously used formalin-inactivated viral vaccine preparations. Ray et al., *J. Infect. Dis.*, 152: 1219–30 (1985). Studies conducted using this new subunit vaccine have shown that a single subcutaneous immunization affords complete protection from challenge infection. Id. It was also found that the isolated viral glycoprotein subunit vaccine, composed of a glycoprotein-lipid complex vesicle, was easier to prepare as compared with subunit vaccines heretofore proposed. The latter are typically isolated in such a way as to be rendered lipid free. See, for example, U.S. Pat. Nos. 4,344,935, or 4,356,169 and Morein et al., *J. Gen. Virol*, 64: 1557–69 (1983). That a glycoprotein lipid complex has shown such exceptional ability to confer immunity is considered quite surprising, as lipids are generally regarded as non-antigenic and thus their presence in a vaccine composition would be thought to reduce its immunogenic effectiveness.

Our viral glycoprotein subunit vaccine, its method of preparation and method of use are the subject of U.S. patent application Ser. No. 798,536, now U.S. Pat. No. 4,790,987, issued Dec. 13, 1988.

The preparation of our subunit vaccine is carried out in such a way that the antigenic sites essential for obtaining the desired antibody response are not chemically altered, with the result that antigenicity is not compromised. Further, our vaccine preparation is free of any viral genome and so avoids the risk of infection. Accordingly, our subunit vaccine offers distinct advantages over chemically inactivated virus and modified live virus vaccines. Insofar as is known, however, intranasal administration of a viral coat subunit vaccine has not been proposed heretofore as an effective means for affording protection against infection. Because subunit vaccines include none of the viral genome, neither clinical nor sub-clinical infection could result from administration of such a vaccine. Thus, the knowledge on which previous intranasal, modified live virus vaccines was predicated would not have suggested that a subunit vaccine such as ours, which is comprised of two envelope glycoproteins and the lipid bi-layer from the virus, could induce immunity by intranasal administration.

BRIEF DESCRIPTION OF THE INVENTION

In accordance with the present invention, there is provided a method for the intranasal administration of a viral glycoprotein subunit vaccine which gives rise to a protective immune response in recipients of the vaccine. Both systemic and local antibody responses to the viral glycoprotein subunit vaccine are elicited after intranasal immunization. This result stands in sharp contrast to that obtained by subcutaneous immunization with the same antigen dosage, which markedly increases the systemic antibody response, but elicits only a moderate local response in the bronchial tract and thus produces only limited protection from infection.

BRIEF DESCRIPTION OF THE DRAWINGS

Referring to the drawings herein.

DETAILED DESCRIPTION OF THE INVENTION

Figure 1:
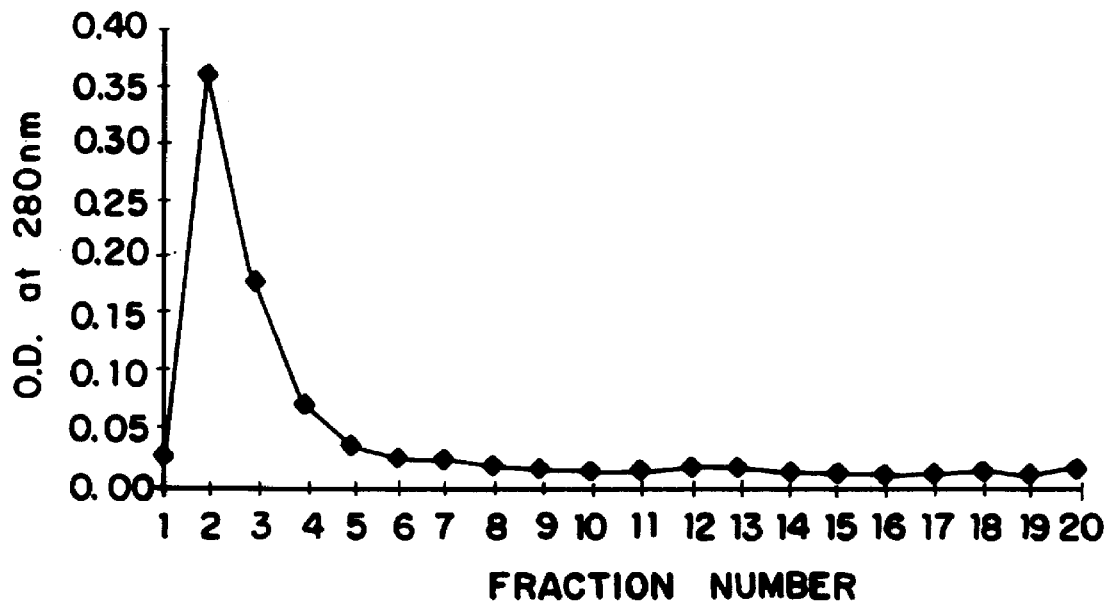
FIG. 1 shows the elution profile of hamster serum protein bound to a column of immobilized jacalin, eluted with melibiose (0.1M).

Any lipid-containing virus which has an antigenic glycoprotein component constitutes suitable material for use in the method of the present invention. The lipid component of the glycoprotein-lipid complex is derived from the host cells in which the virus is produced. The lipids are incorporated into the viral envelope, along with the virus-specified proteins, during envelope assembly in the host cell. The manner in which the vaccine is prepared causes the glycoproteins and lipids to form discrete complexes or vesicles. Rather than being an undesirable component of the resulting glycoprotein subunit vaccine as would be expected, the associated lipids appear to enhance the immunogenicity of the preparation as a whole by acting as an adjuvant. The ability to form the antigenic lipid-glycoprotein vesicles is a function of the chemical nature of glycoproteins and lipids in general, and thus is not restricted to any specific type of glycoprotein or lipid.

Among the better characterized viral glycoproteins, which are generally recognized as being antigenic, are two types which are known generically as receptor-binding glycoproteins and fusion glycoproteins. These are defined by their function in the process of host cell infection, and may be known by different specific names in different viruses. At least one, and frequently both, are present in such well known disease causing agents as paramyxoviruses, influenza viruses, respiratory syncytial viruses, rabies virus, herpes viruses and human immunodeficiency viruses, the latter including the etiologic agent of acquired immune deficiency syndrome (AIDS).

Particularly well-characterized are the receptor-binding-type and fusion-type glycoproteins possessed by all members of the family of paramyxoviridae. Included in this family are the parainfluenza viruses, measles virus, mumps virus, respiratory syncytial virus, Newcastle disease virus, and Sendai virus. In parainfluenza viruses, these glycoproteins are referred to as HN (72,000 daltons) and $F_o$ (54,000 daltons and 20,000 daltons), respectively, and are believed to be responsible for attachment or hemagglutination and neuraminidase activities (HN) and for progress of infection (F) by the virus. Both of these glycoproteins are known to be highly antigenic, and thus are particularly favored for use in practicing the immunization method of the invention. As will be readily apparent, the diseases caused by certain members of the paramyxovirus group, especially parainfluenza, measles and mumps, are very widespread in humans, especially among children, and may be responsible for causing unusually harmful symptoms and/or side effects in afflicted individuals.

The F glycoprotein is known, at least in the case of parainfluenza, to be potentially separable into subunits. For the purposes of the present description, any reference to an F glycoprotein is intended to refer to either the F glycoprotein as a whole, or its individual subunits, all of which may be detergent-solubilized.

Although the method of the invention is described and exemplified herein primarily with reference to subunit vaccine derived from the virus envelope of PI3 virus, the present method is considered to have significantly broader application. It is believed that viral glycoprotein subunit vaccine of the type described herein, when administered intranasally according to the method of this invention, will provide effective protection against a variety of viral infections including, but not limited to, those caused by the family of paramyxoviridae, influenza viruses, herpes viruses, human immunodeficiency viruses and rabies viruses.

The subunit vaccines used in practicing the present invention are readily prepared according to techniques well-known to those skilled in the art. The virus of interest is cultured in a suitable host-cell culture, purified to remove cellular debris and treated with a dialyzable detergent, such as cholate or octyl-D-glucoside to solubilize the desired envelope glycoprotein. It is important that the detergent used be easily dialyzable, to insure that only the detergent will be removed during further processing to the vaccine. After solubilization, the detergent-soluble portion of the virus is separated from the insoluble nucleocapsid by centrifugation, or other suitable means. The supernatant liquid is then dialyzed to produce complexes consisting of endogenous lipids and viral glycoproteins, which constitute the immunogenic agent of the resultant vaccine. A detailed description of the preparation of such a viral glycoprotein subunit vaccine is provided in Ray et al., *J. Infect Dis.*, 152, pp. 1219–30 (1985), (as well as in the aforementioned U.S. Pat. No. 4,790,987) the entire disclosure of which is incorporated by reference in the present application for patent, as if set forth herein in full. The viral glycoproteins may also be produced by genetic engineering (e.g. using recombinant DNA technology) or other techniques for purposes of the invention.

Further purification of the glycoproteins may be achieved by affinity chromaptography. The procedure for preparing monoclonal antibodies to the HN and F glycoproteins of human parainfluenza type 3 virus and the process of using those antibodies in the isolation and purification of the glycoproteins is generally described in Ray et al., *Virology*, 148, pp. 323–36 (1986) and Ray et al., *J. Gen. Virol.*, 68, pp. 409–18, (1987). The disclosure of each of these latter two articles is incorporated by reference in the present application for patent, as if set forth herein in full. Those experienced in the field of the present invention are quite familiar with the techniques for preparing hybridoma cell lines derived by fusing an immortal cell line and lymphocytes sensitized against the immunogenic preparation. Such techniques are described, for example, in Douillard, J-Y. and Hoffman, T., *Basic Facts About Hybridomas*, in: *Compendium of Immunology*, Vol. II, L. Schwartz (ed.) (1981); Kohler, G. and Milstein, C., *Nature* 256, 495–497 (1975); *European Journal of Immunology*, Vol. 6 pp. 511–519 (1986), Koprowski et al., U.S. Pat. No. 4,172,124, and Koprowski et al., U.S. Pat. No. 4,196,265, the disclosures of which are also incorporated by reference herein.

In this particular instance, BALB/C mice were immunized with virus disrupted by repeated freezing and thawing (10 times each). A total of five im immunizations with 10 µg of viral protein each was administered at three-day intervals. The first immunization contained Freund's complete adjuvant. Lymph node cells were fused with myeloma cells by using polyethylene glycol 4,000, three days after the last injection [Kearney, J. F. et al., A new mouse myeloma cell line that has lost immunoglobulin expression but permits the construction of antibody-secreting hybrid cell lines. J. Immunol., 123: 1548–50 (1979)]. Fused cells were cultured in RPMI 1640 medium containing field calf serum (15%), 2-mercaptoethanol (0.4%), glutamine (292 µg/ml). hypoxanthine (13.6 µg/ml), aminopterin (0.17 µg/ml), and thymadine (0.38 µg/ml). Culture fluids from growing colonies were initially screened by ELISA with disrupted virions as antigen. Cultures showing reactivity to viral antigens were cloned by limiting dilution in microtiter plates. Culture fluids from cloned cells were further tested to ascertain their antibody specificity by immunofluorescence, HAI, neuraminidase inhibition, neutralization of infectivity, and immune precipitation tests. The isotype was determined by ELISA with the use of alkaline phosphatase-conjugated goat antibodies specific for mouse isotypes (Southern Biotechnology Associates, Birmingham, Ala.). Hybridoma cells were innoculated ip into mice for large-scale preparation of antibodies from ascites fluid.

The actual tests employed in determining antibody specificity and isotype classification are described in the aforementioned U.S. Pat. No. 4,790,987.

Regarding specific procedures for performing affinity chromatography, a summary of conventional techniques is provided in Goding, J. W., *Monoclonal Antibodies: Principles and Practice*, Academic Press, (1983).

Prior to purifying the envelope glycoproteins by affinity chromatography, the two aforementioned monoclonal antibodies to PI 3, 13.5.9.6.2 (anti-HN) and 9.4.3 (anti-F) were immobilized to Sepharose 4B matrix. Immunoglobulin portions from ascites fluids were prepared by 50% (w/v, final concentration) ammonium sulphate precipitation. The precipitate was dissolved and dialyzed against 0.1M-NaHCO$_3$, 0.5M-NaCl, pH 8.3, with frequent changes. Finally, the immunoglobulin portions were separately coupled to CNBr-activated Sepharose 4B-ig matrix were blocked with 0.1M-Tris-HcCl pH 8.0 and the gel was washed three times successively with 0.1M-Tris-HCl, 0.5 M-NaCl, pH 8.9 and 0.1M-sodium acetate, 0.1M-NaCl, pH 4.0 to remove uncoupled protein. The ligand concentration in the Sepharose 4B matrix was determined spectrophotometrically at 280 nm by suspending the coupled gel in ethylene glycol or solubilizing in 0.1M-NaOH, 0.1% (w/v) NaBH$_4$ at 75° C. (Dean, P. D. G. et al., Affinity Chromatography, A Practical Approach, p. 75, Washington, D.C.: IRL Press (1985)).

Detergent-soluble envelope glycoproteins or virus-infected cell lysate were used for adsorption to the antibody-coupled Sepharose 4B matrix. The Sepharose 4B-Ig beads and the lysate of crude virus pellets or infected cells were allowed to mix end-over-end for 4 h at 4° C. Alternatively, the beads were paced in a column and the antigen preparation was passed slowly over the column at a flow rate of 10 ml/h and recycled at least five times. The unadsorbed material was used for purification of the other glycoprotein through a corresponding antibody-coupled Sepharose 4B matrix. The column was washed with 20 vol. washing buffer (10 mM-Tris-HCl pH 8.0, 1 mM-EDTA, 0.1% octyl glucoside; Varsanyi, T. M. et al., Purification, morphology and antigenic characterization of measles virus envelope components, "Journal of General Virology", 65: 355–366 (1984)). Finally, HN or F was eluted with 3M-sodium thiocyanite and dissolved in washing buffer. The eluted material was collected and directly concentrated in a collodian bag (Schleicher & Schull) against several changes of 10 mM-Tris-HCl, 150 mM-NaCl, 0.01% NaN$_3$, pH 7.6.

Purified HN and F glycoproteins, prepared as described above, are useful vaccine components, whether used individually or together. Perferably, however, the two components are combined in an appropriate diluent vehicle or carrier, in the required proportions. Ratios of about 4:1 to about 1:1 HN to F may be employed to provide effective protection against infection.

As noted above, the presence of lipid with the glycoprotein in the vaccine appears to have an unexpected beneficial effect on the stimulation of the recipient's immune response. Although the mechanism underlying the immunogenic effect observed has not been elucidated, it may be that the lipids function as an adjuvant by enhancing the antigenic effect of the glycoproteins. The endogenous lipid present in the viral envelope, when simultaneously extracted with the glycoprotein by the earlier described procedure, is sufficient to evoke an adequate protective level of antibody production. However, if the vaccine is to be prepared from purified, isolated glycoprotein, it may be desirable to add lipid from an external source in order to obtain the same result seen with the unpurified preparation comprising naturally occurring lipid. By preparing the subunit vaccine in this way the original protein-lipid membrane structure is effectively reconstituted. It has been found that addition of the lipid causes spontaneous formation of vesicles, which comprise the two envelope glycoproteins HN and F, and a lipid bi-layer, thus mimicly the product obtained by solubilization of the viral envelope followed by dialysis. This procedure may be carried out simply by dissolving the lipid in a dialyzable detergent solution containing the glycoprotein, and dialyzing the solution as described previously in the solubilization procedure. In this manner, not only is it possible to prepare vesicles by combining purified protein with exogenous lipid, but it is also possible, by addition of lipid to the solubilized protein-lipid preparation, to amplify the effect of the endogenous lipid by increasing the natural lipid: protein ratio. Virtually any source of lipid is acceptable for the reconstitution of the vesicular product. Among the lipids contemplated as useful in the present vaccine are phospholipids, representative examples of which are lecithin, cephalin and sphingomyelin. Particularly preferred is lecithin, especially egg lecithin, a phosphatidyl choline.

The subunit vaccine described above may be formulated for intranasal administration with a pharmaceutically acceptable carrier such as water, buffered saline, ethanol, polyol (for example, glycerol, propylene glycol, liquid polyethylene glycol and the like) suitable mixtures thereof, or vegetable oils. If necessary, the action of contaminating microorganisms may be prevented by various antibacterial and antifungal agents, such as parabens, chlorobutanol, phenol, sorbic acid, thimerosal, and the like. It will often be preferable to include in the formulation isotonic agents, for example, glucose or sodium chloride. Such formulation may be administered intranasally as an aerosol or atomized spray, or as liquid drops.

As used herein, "pharmaceutically acceptable carrier" includes any and all solvents, dispersion media, antibacterial and antifungal agents, isotonic and absorption delaying agents and the like which may be appropriate for intranasal administration of the viral glycoprotein subunit vaccine. The use of such media and agents for pharmaceutically active substances is known in the art. Except insofar as any conventional media or agent is incompatible with the active ingredient, its use in the therapeutic compositions is contemplated. Supplementary active ingredients can also be incorporated into the composition, if necessary or desirable.

It is especially advantageous to formulate the vaccine in dosage unit form for ease of administration and uniformity of dosage. Dosage unit form as used herein refers to a physically discrete unit of vaccine appropriate for the subject to be immunized. Each dosage should contain the quantity of active material calculated to produce the desired therapeutic effect in association with the selected pharmaceutical carrier. Procedures for determining the appropriate vaccine dosage for a given class of recipient are well known to those skilled in art. Generally, when administering a composition comprising the HN and F antigens of the virus, a dosage of about 10–200 µg should be satisfactory for producing the desired immune response.

The glycoprotein-lipid containing viruses are responsible for causing infections in a wide variety of vertebrate hosts, and the above-described subunit vaccine formulations are adaptable for intranasal administration to any vertebrate host which is susceptible to these infections. However, the preferred vaccines of the invention, intended for prevention of parainfluenza infection, are most valuable in treatment of mammalian hosts, including man.

The following examples are provided to describe the invention in further detail. These examples are intended to illustrate and not to limit the invention.

Example 1—Preparation of Vaccine From Human Parainfluenza Type 3 (PI3) Virus

Vaccine was prepared from cultured LLC-$MK_2$ cells (rhesus monkey kidney) according to methods previously described in Ray et al., *J. Infect. Dis.* supra, at 1220–21, with protein estimation determined in the same manner as there indicated. Approximately one-third of the total virus protein could be recovered in the detergent soluble fraction. This material showed a significant HA titer (1:320).

Example 2—Immunization of Test Animals

A—Effect of Dosage on Protection

Three groups of animals (I, II and III) were immunized intranasally at weekly intervals over four consecutive weeks with different doses of the vaccine prepared as described in Example 1, above. The desired quantity of the vaccine in a 100 μl volume was slowly instilled in aliquots through both nostrils. The tongues of the animals were restrained to minimize swallowing of the vaccine until administration was completed. A parallel group of animals was included as an unimmunized control (IV). Twenty-one days after the last immunization, the animals were challenged intranasally with $10^5$ p.f.u. live virus in 100 μl. Infected hamsters were sacrificed at 70 hours after infection and blood was collected for serum preparation.

Bronchial lavages from each hamster were collected by slowly instilling and aspirating 1 ml. of phosphate buffered saline (PBS) with a syringe and 18 gauge needle through the trachea. Bronchial lavages were clarified by centrifugation and stored frozen in aliquots. Trachea and lungs of the animals were aseptically removed, suspended in 2 ml of Dulbecco's medium containing 1% BSA bovine serum albumin and stored frozen until used.

Plaque assays of the hamster lung homogenates were done in accordance with the procedure described in Ray et al., *J. Infect. Dis.,* supra at 1220. No virus was recovered from the lungs of the intranasally immunized test animals after challenge infection.

By contrast, the unimmunized group (IV) of test animals showed virus recovery on the order of $10^4$ p.f.u./gm. of tissue, as previously reported. Id. at 1226–27. The results of the just described immunization test are set forth in Table 1A.

B—Effect of Mode of Administration On Protection

In order to further determine the protective immune response using relatively low quantities of the vaccine and to compare the efficacy of intranasal versus subcutaneous administration, another test was conducted with four more groups of hamsters. The test animals in groups V and VI were immunized four times at weekly intervals with 5 μg. of the vaccine prepared as in Example 1, above, either through the subcutaneous or intranasal routes. The test animals in group VII were immunized intranasally only three time with 5 μg. doses of the vaccine. An unimmunized group of test animals (VIII) was included as a control. This test established that the animals immunized subcutaneously were only partially protected from challenge infection. Virus titers in the lungs of the group V test animals were 100 fold lower than the unimmunized control. On the other hand, using the same quantity of vaccine the animals immunized intranasally showed complete protection from challenge infection. The test animals in group VII also showed only partial protection. The results of this test are set forth in Table 1B.

TABLE 1

Immunization schedule and virus recovery following challenge infection of hamsters with live PI3 virus

| Group No.* | Route of Administration | Immunization doses at weekly intervals (in micrograms) Week 0 | 1 | 2 | 3 | Virus recovery (pfu/gm) from lungs after challenge infection+ |
|---|---|---|---|---|---|---|
| A | | | | | | |
| I | Intranasal | 5 | 5 | 5 | 5 | <10 |
| II | Intranasal | 10 | 10 | 10 | 10 | <10 |
| III | Intranasal | 20 | 20 | 20 | 20 | <10 |
| IV | Unimmunized | — | — | — | — | $4.7 \times 10^4$ |
| B | | | | | | |
| V | Subcutaneous | 5 | 5 | 5 | 5 | $1.9 \times 10^4$ |
| VI | Intranasal | 5 | 5 | 5 | 5 | <10 |
| VII | Intranasal | 5 | 5 | 5 | 5 | $1.2 \times 10^2$ |
| VIII | Unimmunized | — | — | — | — | $4.0 \times 10^4$ |

*Each group consisted of 4 hamsters.
+Virus recovery expressed as the geometric mean titers from four animals.

Example 3—Determination of Local Immune Response

Bronchial lavages were collected after sacrificing the infected hamsters and used in plaque neutralization tests of the PI3 virus on Vero cell monolayers. The plaque nuetralization tests were conducted according to the procedure described in Ray et al., *J. Infect. Dis.*, supra, at 1221–22. The test results, which are expressed as the reciprocal of the highest dilution of serum that inhibits plaque formation by 50%, are set forth in Table 2. These results show that animals immunized subcutaneously four times with 5 μg, or intranasally three times with 5 μg. of the vaccine prepared as in Example 1, above had a two-fold variation in neutralization titers and partial protection from challenge infection. By contrast, animals immunized intranasally four times with 5 μg, 10 μg or 20 μg were found to exhibit reciprocal neutralization titers of 20 or higher in their bronchial lavages and were completely resistant to challenge infection.

Sera and bronchial lavages of the test animals were also tested for anti-HN antibodies by HI assay, according to the procedure set forth in Ray et al., *J. Infect. Dis.,* supra at 1221. The results of these tests are also shown in Table 2. Serum from subcutaneously immunized animals showed a reciprocal titer of 16, whereas bronchial lavages were found to be devoid of HI activity. However, HI activity was detected both in sera and bronchial lavages of animals immunized intranasally with high quantities of glycoproteins (four times with 10 μg. or 20 μg.).

Bronchial lavages were also analyzed by immune precipitation to detect the specificity of local antibody for viral polypeptides. In carrying out this analysis, LLC-$MK_2$ cells were infected with PI3 virus and the infected cells were labeled at 30 hours after infection with $^{35}S$-methionine for 3 hours. Cells were lysed with lysis buffer, centrifuged at 13,000 g. for 5 minutes and the clear lysate was used as the source of viral polypeptides. Bronchial lavage (100 μl) was mixed with the lysate and the immune precipitates were obtained by adding protein A-sepharose CL-4B beads, precoated with goat anti-hamster whole serum. The sepharose beads were extensively washed and analyzed by SDS-PAGE followed by fluorography as generally set forth in Ray et al., J. Infect. Dis, supra, at 1222.

Figure 3:
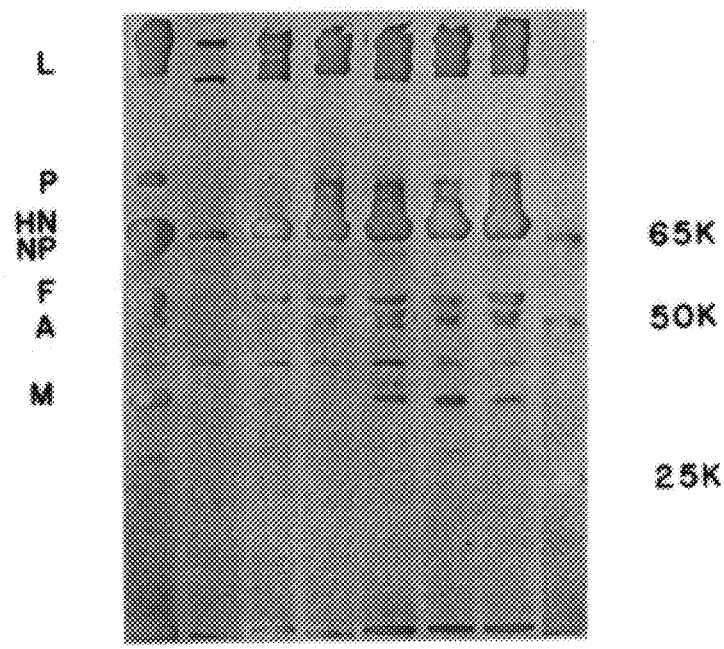
FIG. 3 shows the results of immune precipitation of $^{35}$S-methionine-labeled parainfluenza type 3 virus infected LLC-MK$_2$ cell lysate with bronchial lavages from different test animal groups.

The results of the immune precipitation analysis with representative specimens from each group of hamsters are shown in FIG. 3. The $^{35}$S-methionine labeled polypeptide profile of PI3 virus appears in lane 1 and that of immune precipitates with bronchial lavages from hamsters in groups I and VI appears in lanes 2 to 7, respectively, which were developed on 10% SDS PAGE. Polypeptides of vesicular stomatitis virus were run in lane 8 as molecular weight markers.

The bronchial lavages of hamsters immunized intranasally with different doses of glycoproteins could effectively precipitate both HN and F polypeptides (lanes 4, 5, 6 and 7) and the relative intensity of HN (68K) appeared to be much higher than $F_1$ (54K). It is difficult to quantitate the antibody responses to these glycoproteins from these results, as the higher molecular weight bands (>68K) could not be identified and may represent uncleaved fusion protein (Fo) and aggregated homo-or heteropolymers of HN and F. Bronchial lavages from subcutaneously immunized animals were also found to precipitate both HN and $F_1$, but with much lower intensities (lane 3), when compared with the results from intranasally immunized animals. The finding of the nucleocapsid associated protein M polypeptide in immune precipitates with bronchial lavages from animals intranasally immunized with higher quantities of the glycoproteins (lanes 5, 6 and 7) is presumably due to its presence in the vaccine preparation used for immunization.

TABLE 2

NEUTRALIZATION AND
HI TITERS OF BRONCHIAL LAVAGES AND SERA
OF IMMUNIZED AND CONTROL HAMSTERS*

| Route of Immunization | Doses of Vaccine | Reciprocol HI Titer in Bronchial Lavage | Reciprocal Serum HI titer | Reciprocal Neutralization Titers |
|---|---|---|---|---|
| Intranasal | 5 ug × 3 | 4 | <4 | 10 |
| Intranasal | 5 ug × 4 | 8 | <4 | 20 |
| Intranasal | 10 ug × 4 | 8 | 8 | 40 |
| Intranasal | 20 ug × 5 | 8 | 16 | 40 |
| Subcutaneous | 5 ug × 4 | 4 | 16 | 5 |
| Unimmunized | — | <4 | <4 | <5 |

*Titers determined by using 8 HAU of the virus and expressed as the mean value from four animals.

Example 4—Comparison of Local and Systemic Response

In order to further analyze the immune response an effort was made to detect antibodies to HN and F in sera and bronchial lavages by means of enzyme-linked immunosorbent assay (ELISA). The results of these assays are shown in Table 3. Serum and bronchial lavages were assayed separately to determine the specific antibody responses to HN and F. Affinity purified HN and F were used separately to coat ELISA plates. Antigen coated plates were blocked with 1% BSA in borate-saline before addition of the test specimens. Serial two-fold dilutions of serum or bronchial lavage were incubated with antigen coated wells. Rabbit anti-hamster whole serum was used as the second antibody to determine the total Ig response to viral glycoproteins. The IgA class specific antibody response was determined by using rabbit anti-serum to hamster IgA.

The hamster IgA required for preparation of rabbit antisera to hamster IgA was prepared from pooled sera by lectin affinity chromatography using jacalin (Pierce Chemical Co., Rockford, Ill.). Jacalin, an α-D-galactose-binding lectin, is extracted from jack-fruit seeds and has been observed to bind specifically with human IgA. Immobilized jacaline on agarose beads was packed in a small disposable plastic column (Biorad Laboratories, Richmond, Calif.) up to a volume of 4 ml. The column was washed with about 5 column volumes of PBS, pH 7.4. Pooled hamster sera (6 ml.) was dialyzed against PBS and slowly recycled four times through a jacalin column. The column was washed with ten volumes of PBS and the bound protein was eluted with 0.1M melibiose (Sigma Chemical Co., St. Louis, Mo.) in PBS and fraction were monitored for absorbance at 280 mm. Eluted fractions were combined and concentrated in a collodion bag (Schleicher and Schuell, Keene, N.H.).

Figure 2:
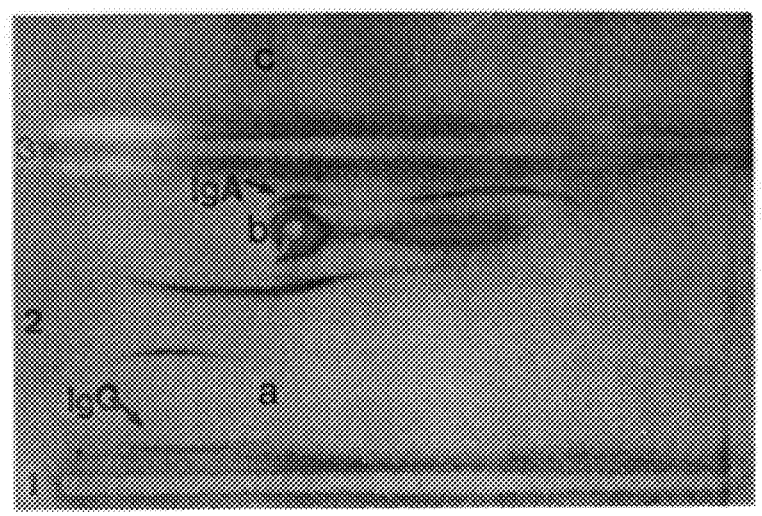
FIG. 2 shows an immunoelectrophoretic pattern resulting from the analysis of rabbit antiserum to hamster IgA.

Hamster serum protein bound to the jacalin column was eluted as a sharp peak with melibiose FIG. 1. Rabbit antiserum raised against the purified protein showed one strong precipitin line in an immunodiffusion test. An additional weak precipitin band was also observed due to the presence of contaminating serum proteins eluted from the jacalin column (not shown). Further analysis by immunoelectrophoresis (IEP) demonstrated that the rabbit antiserum cross-reacted with hamster IgG (H and L-chain specific). This cross-reactivity was eliminated by repeated adsorption of the rabbit antiserum through a Sepharose 4B-hamster IgG column and monitored by IEP (FIG. 2) and ELISA against purified hamster IgG. As appears in FIG. 2, rabbit antiserum to purified IgA (trough 1) and the adsorbed antiserum to hamster IgG (trough 3) were allowed to react with electrophoresed hamster IgG (wells a and c) and hamster whole serum (well b), respectively. Goat antiserum to hamster IgG was used as a control (trough 2). Positions of precipitation arcs which appeared with hamster IgA and IgG are indicated by arrows. The trailing part of the precipitation arc appearing with IgA is probably due to contaminating hamster serum protein present in the IgA preparation from the jacalin column.

The IgA thus obtained was used to raise hyperimmune rabbit antisera. Rabbits were immunized three times intramuscularly each with 100 μg. of purified IgA at weekly intervals. The first immunization was offered by emulsifying the protein with Freunds complete adjuvant (Difco Laboratories, Detroit, Mich.). A second immunization was given similarly with Freund's incomplete adjuvant and the third immunization, with the purifed IgA without adjuvant, was given intramuscularly with a similar quantity of protein. Rabbits were immunized intravenously with another 100 μg. of purified IgA and sacrificed by cardiac puncture on the fourth day after the last immunization for preparation and storage of antisera. The antiserum was recycled four times through a column of SEPHAROSE-4B coupled with hamster IgG (H & L chain specific) (Southern Biotechnology Associates, Birmingham, Ala.) to adsorb out its cross-reactivity with hamster IgG. The rabbit antiserum was analyzed by immunodiffusion, immunoelectrophoresis and ELISA to determine its specificity for hamster IgA.

After incubation with second antibody, goat anti-rabbit Ig conjugated wth alkaline phosphatase was added to the wells of the ELISA plates. Finally, p-nitrophenyl phosphate was used as the substrate to develop a color reaction and after incubation the reaction was stopped by addition of an equal volume of 2(N) NaOH. Color intensities were measured at 405 nin with a spectrophotometer (Titertek Multiskan $^R$MC, Flow Laboratories, McLean, Va.). Total IgA titers in bronchial wash were measured by coating the plate with jacalin or goat anti-hamster whole serum (Cappel Philadelphia, Pa.) and using rabbit anti-hamster IgA as the second antibody. All the ELISA reagents were previously titrated against their counterparts to determine the appropriate dilution to be employed.

According to the results of the ELISA determination, as shown in Table 3, test animals immunized subcutaneously with vaccine preparation as described in Example 1, above, showed a rise in antibody titers in sera but low levels in bronchial lavages. On the other hand, higher antibody responses were observed in bronchial lavages of intranasally immunized hamsters, and the titers increased with an increase in dose of the glycoproteins (groups C, D, E and F). The appearance of glycoprotein specific antibodies as well as IgA class specific responses to both HN and F could be detected in sera and bronchial lavages with intranasally immunized animals. It is interesting to note that intranasal immunization with a higher quantity of vaccine also gives rise to a systemic antibody response, since animals immunized four times with 20 $\mu$g. had similar Ig and IgA levels of serum antibodies as were observed in subcutaneously immunized group of animals. ELISA titers of antibodies in bronchial lavages were found to be low, which may be due to dilution of the bronchial fluids during their collection.

Figure 4:
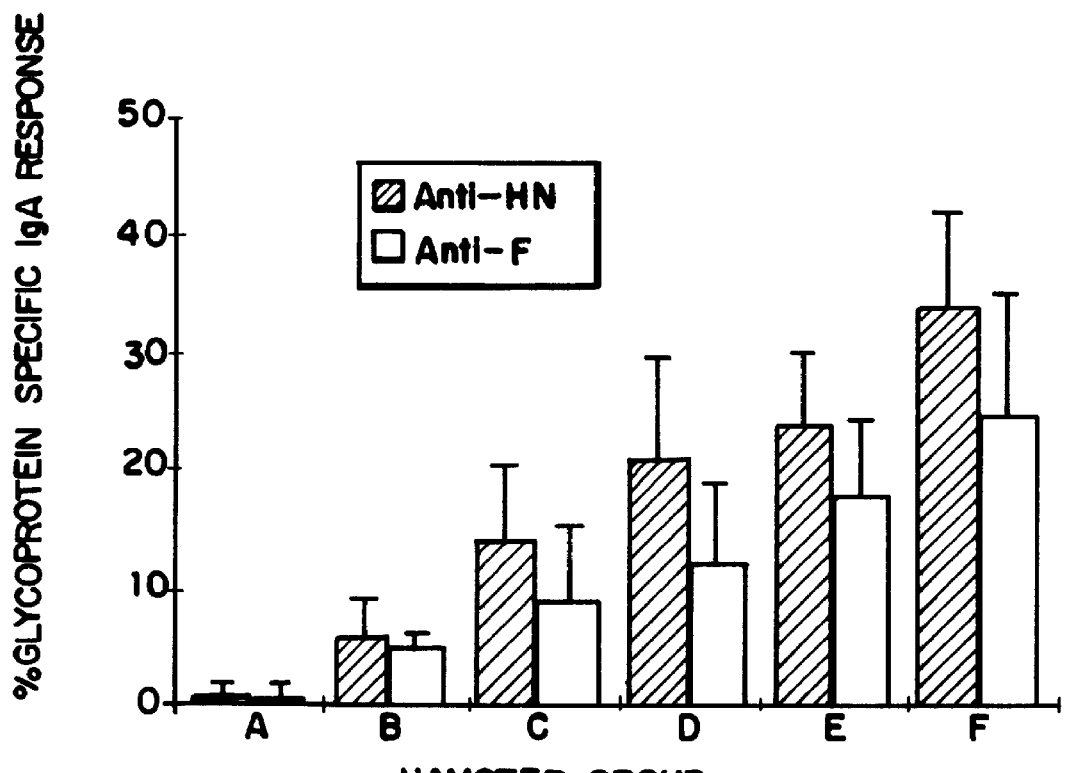
FIG. 4 graphically represents the relative amounts of IgA class-specific antibodies to virus envelope glycoproteins appearing in bronchial lavages of control and immunized test animals after challenge with parainfluenza type 3 virus.

Further efforts were made to determine the relative proportions of antigen specific IgA and total IgA in bronchial lavages. To determine total IgA titers, bronchial lavages were tested separately with two different reagents, jacalin and goat anti-hamster whole serum, coated on ELISA plates. Similar titers were obtained with both of these reagents. Glycoprotein specific IgA titers in bronchial lavages were determined separately to affinity purified HN and F and results are shown in FIG. 4, in which optical densities are plotted against dilutions of each bronchial lavage to determine linear portions of the graph for both antigen specific and total IgA titrations. The ratios of the optical densities of antigen specific and total IgA, at a fixed dilution of the two titrations, were multiplied by 100 to represent the relative percentage of antigen specific IgA in bronchial lavage. Anti-HN and anti-F antibody level of animals which were unimmunized (group A), subcutaneously immunized four times with 5 $\mu$g. (group B), intranasally three times with 5 $\mu$g. (group C), four times with 5 $\mu$g. (group D), four times with 10 $\mu$g. (group E) or four times with 20 $\mu$g. (Group F) of vaccine are shown by bar diagram. Upper bars represent the variation within a group of animals.

From FIG. 4 it can be seen that intranasally immunized animals exhibited a significantly higher local IgA response to HN (>15%) and F (>7%) glycoproteins and the anti-HN IgA response was greater than anti-F. Bronchial lavages were also tested against disrupted virus coated on an ELISA plate, and similar IgA responses were also observed. It appeared from a similar experiment that other classes of antigen specific immunoglubins were present in much lower titers.

The test results set forth in the foregoing examples indicate that the above-described glycoprotein subunit vaccine can effectively induce protective immune response in the respiratory tract following administration through the intranasal route. This appears to be due, at least in part, to induced local antibody production, particularly antibody of the IgA class. The above data further indicate that intranasal immunization requires low quantities of the viral envelope glycoprotein and lipid complex, as compared with subcutaneous administration, in order to confer effective protection from challenge infection.

While certain preferred embodiments of the present invention have been described above, it is not intended to limit the invention to such embodiments, but various modifications may be made thereto, without departing from the scope and spirit of the present invention, as set forth in the following claims.

TABLE 3

ELISA TITERS OF VACCINE-INDUCED SPECIFIC ANTIBODY IN SERUM AND BRONCHIAL LAVAGES OF TEST ANIMALS*

| Route of Immunization | Dose of Vaccine | Serum IG Response | | Serum IgA Response | | Local IG Response | | Local IgA Response | |
|---|---|---|---|---|---|---|---|---|---|
| | | Anti-HN | Anti-F | Anti-HN | Anti-F | Anti-HN | Anti-F | Anti-HN | Anti-F |
| Intranasal | 5 ug × 3 | 800 | 400 | 400 | 200 | 100 | 50 | 20 | 10 |
| Intranasal | 5 ug × 4 | 800 | 400 | 400 | 200 | 200 | 100 | 40 | 20 |
| Intranasal | 10 ug × 4 | 800 | 400 | 400 | 200 | 200 | 100 | 40 | 20 |
| Intranasal | 20 ug × 4 | 1,600 | 800 | 800 | 800 | 400 | 200 | 80 | 80 |
| Subcutaneous | 5 ug × 4 | 3,200 | 1,600 | 800 | 400 | 50 | 50 | 5 | 5 |
| Unimmunized | — | <100 | <100 | <100 | <100 | <50 | <50 | <5 | |

*Titers expressed as the means reciprocals of highest dilution of samples for four animals showing positive reactivity (O.D. = 0.3).

What is claimed is:

1. A method for immunizing against human respiratory viral infection comprising steps of providing a viral envelope subunit vaccine, said viral envelope being from a virus selected from the group consisting of human influenza viruses, parainfluenza viruses, mumps virus, measles virus and respiratory syncytial virus and comprising a glycoprotein selected from receptor-binding glycoproteins, fusion glycoproteins and combinations thereof, complexed with a lipid and intranasally administering said vaccine to a human host sought to be immunized against said respiratory viral infection.

2. The method as claimed in claim 1, wherein said glycoprotein is an F glycoprotein and an HN glycoprotein.

3. The method as claimed in claim 1, wherein said glycoprotein is an F glycoprotein and an HN glycoprotein reconstituted into lipid vesicles.

4. The method as claimed in claim 1, wherein said viral envelope subunit vaccine is produced by genetic engineering.

5. In combination, a dispenser for dispensing the contents thereof as an aerosol, atomized spray or liquid drops and a composition, contained in said dispenser, for intranasal administration to immunize against human respiratory viral infection, said composition comprising an immunogenically effective amount of a viral envelope subunit vaccine, said viral envelope being from a virus selected from the group consisting of human influenza viruses, parainfluenza viruses, mumps virus, measles virus and respiratory syncytial virus and comprising a glycoprotein selected from receptor-binding glycoproteins, fusion glycoproteins and combinations thereof complexed with a lipid, and a therapeutically acceptable carrier suitable for intranasal administration.

6. A combination as claimed in claim 5, wherein the composition is in unit dosage form comprising 10–200 micrograms of said vaccine.

* * * * *